United States Patent [19]

Lavielle et al.

[11] Patent Number: 5,436,343
[45] Date of Patent: Jul. 25, 1995

[54] ALKENECARBOXYLIC ACID COMPOUNDS

[75] Inventors: Gilbert Lavielle, La Celle Saint Cloud; Patrick Hautefaye, Servon Brie Comte Robert; Michel Laubie, Vaucresson; Tony Verbeuren, Vernouillet, all of France

[73] Assignee: Adir et Compagnie, Courbevoie, France

[21] Appl. No.: 62,080

[22] Filed: May 14, 1993

[30] Foreign Application Priority Data

May 15, 1992 [FR] France .................. 92 05905

[51] Int. Cl.$^6$ .................. C07D 211/04; A61K 31/445
[52] U.S. Cl. ..................... 546/206; 546/248; 546/335; 549/77; 562/427; 562/430; 562/439; 562/443; 562/444; 562/449; 562/503; 562/504; 562/505; 562/507; 562/556; 562/560; 554/88; 554/106; 554/110
[58] Field of Search ............. 546/206, 248, 335; 549/77; 562/427, 430, 439, 443, 444, 449, 503, 504, 505, 507, 556, 560; 514/331, 357, 438, 561, 562, 564; 554/88, 106, 110

[56] References Cited

U.S. PATENT DOCUMENTS

| | | | |
|---|---|---|---|
| 4,948,808 | 8/1990 | Witte et al. | 514/538 |
| 4,981,873 | 1/1991 | Witte et al. | 514/562 |
| 5,280,043 | 1/1994 | Cooper et al. | 514/562 |

OTHER PUBLICATIONS

Vemylen et al., *Thromboxane Synthase Inhibitors and Receptor Antagonists*, Cardiovascular Drugs and Therapy 1992:6, 29–33 (1992).
Smith, *Role of Thromboxane Receptor Antagonists in Cardiovascular Disease*, in Prostaglandins in Clinical Research: Cardiovascular System, 29–38 (Mar. 1989).
McKenniff et al., *BAY u3405, a Potent and Selective Thromboxane $A_2$ Receptor Antagonist on Airway Smooth Muscle In Vitro*, Br. J. Pharmacol. 104, 585–590 (Aug. 1991).
Ogletree et al., *Pharmacological Profile of BMS 180,291: A Potent, Long–Acting, Orally Active Thromboxane $A_2$/Prostaglandin Endoperoxide Receptor Antagonist*, The Journal of Pharmacology and Experimental Therapeutics 264 No. 2, 570–578 (May 1993).

Primary Examiner—José G. Dees
Assistant Examiner—Dwayne C. Jones
Attorney, Agent, or Firm—Gordon W. Hueschen

[57] ABSTRACT

Compounds of formula (I):

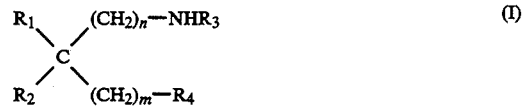

in which:

$R_1$ and $R_2$, which may be identical or different, represent a linear or branched ($C_1$–$C_6$) alkyl radical, a substituted or unsubstituted phenyl radical, a pyridyl radical or a thienyl radical, or, with the carbon atom to which they are attached, a substituted or unsubstituted ($C_4$–$C_7$) cycloalkyl ring, $R_3$ represents
 a substituted or unsubstituted phenylsulfonyl radical,
 a linear or branched ($C_1$–$C_6$) alkyl radical,
 an alkylaminocarbonyl radical,
 or a linear or branched ($C_1$–$C_6$) acyl radical, $R_4$ represents any one of the radicals:

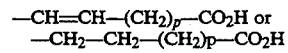

in which p is equal to 0, 1, 2 or 3, n and m, which may be identical or different, represent 0, 1 or 2, their isomers, enantiomers, diastereoisomers and epimers as well as their addition salts with a pharmaceutically acceptable acid or base.

11 Claims, No Drawings ced
ALKENECARBOXYLIC ACID COMPOUNDS

FIELD OF THE INVENTION

The present invention relates to new alkenecarboxylic acid compounds.

More especially, the compounds described in the present invention possess antithromboxane $A_2$ properties, both as thromboxane $A_2$ (TXA$_2$) receptor antagonists and as inhibitors of the activity of the enzyme responsible for thromboxane $A_2$ synthesis: thromboxane $A_2$ synthase.

BACKGROUND OF THE INVENTION

Thromboxane $A_2$ is an arachidonic acid metabolite produced by blood platelets, which causes considerable constriction of blood vessels and induces platelet aggregation. Thromboxane $A_2$ production is increased in disorders such as angina pectoris or cerebrovascular accident, and it plays a very important part in all processes leading to thrombotic disorders.

It was hence especially advantageous to synthesize substances capable of inhibiting the aggregation-promoting and vasoconstrictor activities of thromboxane $A_2$, either as thromboxane $A_2$ receptor antagonists, or as thromboxane $A_2$ synthase inhibitors.

Alkenecarboxylic acid compounds possessing antithrombotic properties have been described in the literature. This applies, in particular, to the compounds described in Patent EP 405,391. The compounds described in the present invention, apart from the fact that they are new, possess pharmacological properties that are markedly more intense than those of the other compounds described in the prior art.

They are hence useful as thromboxane $A_2$ antagonists and as thromboxane $A_2$ synthase inhibitors in the treatment or prevention of thrombotic disorders such as vascular accident. These thrombaxe $A_2$ antagonists also possess properties of protecting the stomach wall (M. L. OGLETREE et al, J. Pharm. and Exp. Therap., 263 (1), 374–380).

DETAILED DESCRIPTION OF THE INVENTION

More specifically, the present invention relates to the compounds of formula (I):

$$\begin{array}{c} R_1 \\ \diagdown \\ \phantom{R}C \\ \diagup \phantom{R} \diagdown \\ R_2 \phantom{XX} (CH_2)_m-R_4 \end{array} \begin{array}{c} (CH_2)_n-NHR_3 \end{array} \qquad (I)$$

in which:

$R_1$ or $R_2$, which may be identical or different, represent a linear or branched ($C_6$–$C_6$) alkyl radical, a phenyl radical (unsubstituted or substituted with one or more halogen atoms or a linear or branched ($C_6$–$C_6$) alkyl, linear or branched ($C_6$–$C_6$) alkoxy, hydroxyl or trihalomethyl radical), a pyridyl radical or thienyl radical, or, with the carbon atom to which they are attached, form a ($C_4$–$C_7$) cycloalkyl ring (unsubstituted or substituted with a linear or branched ($C_6$–$C_6$) alkyl radical), a benzo($C_4$–$C_7$ cycloalkyl) ring-system or a 4-piperidyl ring (unsubstituted or substituted on the nitrogen of the piperidine with a phenylsulfonyl group which is itself optionally substituted with one or more halogen atoms or alkyl groups), $R_3$ represents a phenylsulfonyl radical, unsubstituted or substituted on the phenyl ring with a halogen atom or linear or branched ($C_6$–$C_6$) alkyl radical, a naphthylsulfonyl radical, a linear or branched ($C_1$–$C_6$) alkyl radical, an alkylaminocarbonyl radical, or a linear or branched ($C_6$–$C_6$) acyl radical, $R_4$ represents any one of the radicals:

$$-CH=CH-(CH_2)_p-CO_2H \text{ or}$$
$$-CH_2-CH_2-(CH_2)_P-CO_2H$$

in which p is equal to 0, 1, 2 or 3, n and m, which may be identical or different, represent 0, 1 or 2, their isomers, enantiomers, diastereoisomers and epimers as well as their addition salts with a pharmaceutically acceptable acid or base.

Among pharmaceutically acceptable acids, hydrochloric, sulfuric, tartaric, maleic, fumaric, methanesu/-fonic and camphoric acids, and the like, may be mentioned without implied limitation. Among pharmaceutically accetpable bases, sodium hydroxide, potassium hydroxide, tert-butylamine, diethylamine, ethylenediamine, etc., may be mentioned without implied limitation.

When the compounds of formula (I) possess a radical $R_4$=—CH=CH—(CH$_2$)p—CO$_2$H, the preferred compounds of the invention are those for which the configuration of the double bond of the radical $R_4$ is cis.

The invention also encompasses the process for preparing the compounds of formula (I), wherein the starting material used is: 1/a nitrile of formula (II):

$$\begin{array}{c} R_1 \\ \diagdown \\ \phantom{XX}CH-CN \\ \diagup \\ R_2 \end{array} \qquad (II)$$

in which $R_1$ and $R_2$ have the same meaning as in the formula (I), which is reacted:

with the bromo compound of formula (III) in the presence of lithium diisopropylamide in tetrahydrofuran:

$$\begin{array}{c} \phantom{XXXXX} OCH_3 \\ \phantom{XXXX} \diagup \\ Br-(CH_2)_x-CH \\ \phantom{XXXX} \diagdown \\ \phantom{XXXXX} OCH_3 \end{array} \qquad (III)$$

in which x represents n, n−1 or m according to the compound of formula (I) which it is desired to obtain, to yield the compound of formula (IV):

$$\begin{array}{c} R_1 \phantom{XX} CN \\ \diagdown \phantom{X} \diagup \\ \phantom{XX}C \\ \diagup \phantom{X} \diagdown \phantom{XXXXX} OCH_3 \\ R_2 \phantom{XX} (CH_2)_x-CH \\ \phantom{XXXXXXXXX} \diagdown \\ \phantom{XXXXXXXXXX} OCH_3 \end{array} \qquad (IV)$$

in which x has the same meaning as above, which is either reduced using four equivalents of lithium aluminum hydride in ether to yield the compound of formula (V):

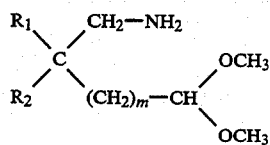  (V)

in which m has the same meaning as in the formula (I), which is converted to the compound of formula (VII):

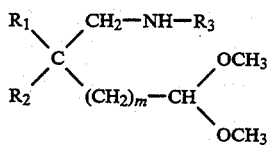  (VII)

in which $R_1$, $R_2$ and m have the same meaning as in the formula (I), by reaction, depending on the nature of $R_3$:
with a halogenated compound of formula (VI) in the presence of triethylamine in toluene:

R'₃X    (VI)

in which X represents a halogen atom and R'₃ represents a substituted or unsubstituted phenylsulfonyl radical or an acyl radical,
with an isocyanate of formula R″N=C=O (VI′) in which R″ represents an alkyl radical, and in this case the radical $R_3$ of the formula (VII) is an alkylaminocarbonyl radical,
an aldehyde of formula R″₃CHO (VI″) in which R″₃ is an alkyl radical, to form an imine which is then reduced to the corresponding amine, which compound of formula (VII) is:
either converted to the aldehyde of formula (VIIIa) in the presence of formic acid:

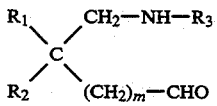  (VIIIa)

in which $R_1$, $R_2$ and m have the same meaning as in the formula (I),
or, when m represents 1 or 2, cyclized under reflux of toluene to the compound of formula (VIIIb), in the presence of paratoluenesulfonic acid:

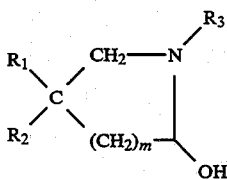  (VIIIb)

in which $R_1$, $R_2$, $R_3$ and m have the same meaning as above, which compound of formula (VIIIa) or (VIIIb) is reacted with the phosphorus ylide of formula (IX), prepared by reaction of the corresponding phosphonium salt in the presence of potassium tert-butanolate in tetrahydrofuran, $(C_6H_5)_3P=CH-(CH_2)_p-CO_2H$    (IX)

in which p has the same meaning as in the formula (I), to yield the compound of formula (I/a), a special case of the compounds of formula (I):

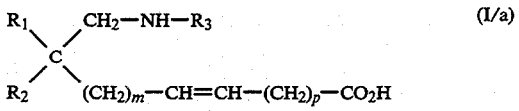  (I/a)

or converted to the corresponding aldehyde of formula (X) using three equivalents of diisobutylaluminum hydride in toluene,

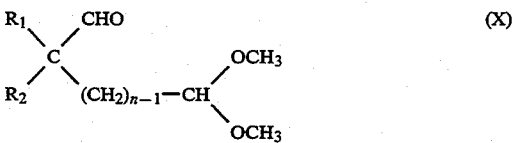  (X)

in which n has the same meaning as in the formula (I), which is reacted with the phosphorus ylide of formula (IX) defined above, to yield, after treatment with diazomethane, the compound of formula (XI):

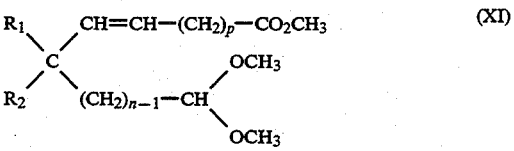  (XI)

in which $R_1$, $R_2$, p and n have the same meaning as above, which, after hydrolysis of the acetal, reduction of the aldehyde formed to an alcohol and formation of the corresponding amine, is converted to the compound of formula (I/b), a special case of the compounds of formula (I), by reacting either the halogenated compound of formula (VI), or the isocyanate of formula (VI′), or the aldehyde of formula (VI″), according to the nature of the radical $R_3$ which it is desired to obtain, and saponifying the ester obtained,

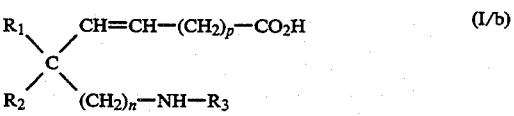  (I/b)

2/ an ester of formula (XII):

  (XII)

in which $R_1$ and $R_2$ have the same meaning as in the formula (I), which is reacted with the bromo compound of formula (III) defined above, to yield the compound of formula (XIII):

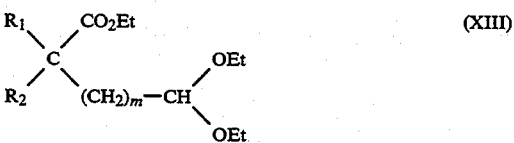  (XIII)

in which $R_1$ and $R_2$ have the same meaning as in the formula (I), which is converted:

a to the corresponding amine of formula (XIV), via the corresponding azide and then the corresponding isocyanate, or via the corresponding acid and the corresponding benzyloxycarbonylamine,

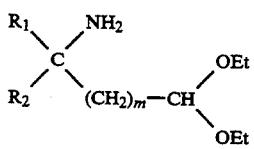 (XIV)

in which $R_1$ and $R_2$ have the same meaning as in the formula (I), on which the same reactions are carried out as those described above for converting the compound (V) to the compound (VII), to yield the compound of formula (XV):

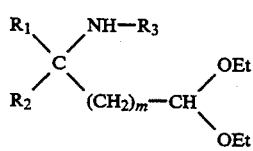 (XV)

in which $R_1$, $R_2$ and m have the same meaning as in the formula (I), which is either converted to the aldehyde of formula (XVIa) in the presence of formic acid:

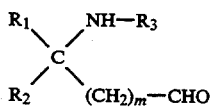 (XVIa)

in which $R_1$ and $R_2$ have the same meaning as in the formula (I), or, when m=2, cyclized under reflux of toluene to the compound of formula (XVIb), in the presence of p-toluenesulfonic acid:

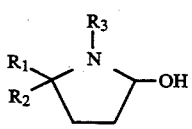 (XVIb)

in which $R_1$, $R_2$ and $R_3$ have the same meaning as above, which compound of formula (XVIa) or (XVIb) is reacted with the ylide of formula (IX) described above, to yield the compound of formula (I/c), a special case of the compounds of formula (I),

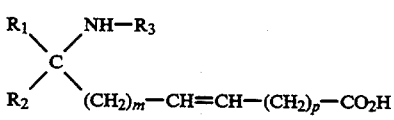 (I/c)

in which $R_1$, $R_2$, $R_3$ and m have the same meaning as in the formula (I), b to the corresponding alcohol of formula (XVII) using an excess of lithium aluminum hydride,

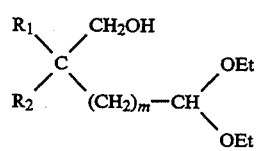 (XVII)

in which $R_1$, $R_2$ and m have the same meaning as in the formula (I), and is then, after intermediate formation of the mesylate, converted to the corresponding nitrile of formula (XVIII):

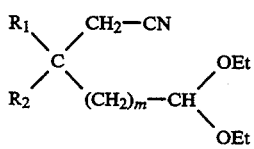 (XVIII)

in which $R_1$, $R_2$ and m have the same meaning as in the formula (I), which is reduced to the corresponding amine of formula (XIX):

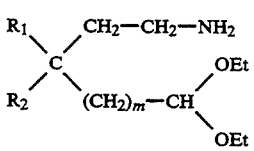 (XIX)

in which $R_1$, $R_2$ and m have the same meaning as in the formula (I), on which the same reactions are carried out as those described above for converting the compound (V) to the compound (VII), to yield the compound of formula (XX):

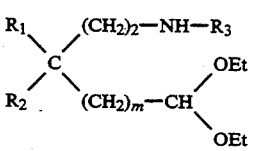 (XX)

in which $R_1$, $R_2$, $R_3$ and m have the same meaning as in the formula (I), which, either after deprotection with formic acid, or cyclization under reflux of toluene in the presence of p-toluenesulfonic acid (when m represents 1 or 2), and then reaction of the ylide of formula (IX) described above, is converted to the compound of formula (I/d), a special case of the compounds of formula (I),

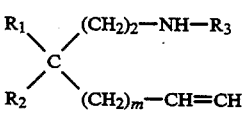 (I/d)

in which $R_3$, m and p have the same meaning as in the formula (I), which compounds of formulae (I/a), (I/b), (I/c) or (I/d) are reduced, if so desired, by catalytic hydrogenation to yield the compounds of formulae (I/a$_1$), (I/b$_1$), (I/c$_1$) or (I/d$_1$) respectively, special cases of the compounds of formula (I),

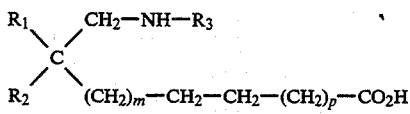 (I/a₁)

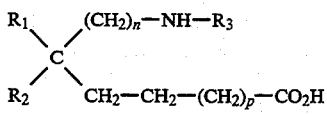 (I/b₁)

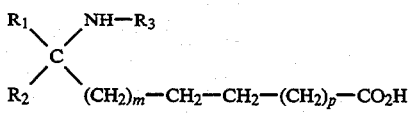 (I/c₁)

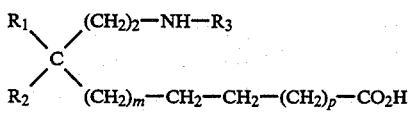 (I/d₁)

in which formulae $R_1$, $R_2$, m, n and p have the same meaning as in the formula (I),
which compounds of formulae (I/a), (I/a₁), (I/b), (I/b₁), (I/c), (I/c₁), (I/d) or (I/d₁):
are purified according to standard purification techniques,
are separated, where appropriate, into their isomers, according to standard separation techniques,
are converted, if so desired, to their addition salts with a pharmaceutically acceptable acid or base.

Furthermore, the compounds corresponding more specifically to the formula (I'), a special case of the compounds of formula (I)

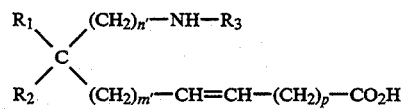 (I')

in which $R_1$, $R_2$, $R_3$ and p have the same meaning as in the formula (I),
n' = 1 or 2
m' = 1 or 2
may also be obtained using the process wherein the starting material used is a compound of formula (XXI):

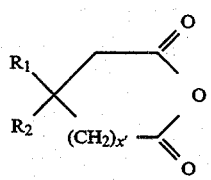 (XXI)

in which $R_1$ and $R_2$ have the same meaning as in the formula (I') and x' is equal to 0 or 1, which is reduced in the presence of sodium borohydride in methanol to yield the compound of formula (XXII):

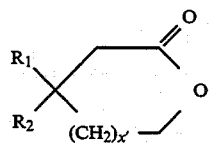 (XXII)

in which $R_1$, $R_2$ and x' have the same meaning as above, which is subjected to the action: either of diisobutylaluminum hydride in toluene, to yield the compound of formula (XXIII):

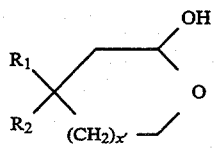 (XXIII)

in which $R_1$, $R_2$ and x' have the same meaning as above, which is reacted with phosphorus ylide of formula (IX):

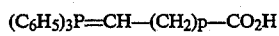
$(C_6H_5)_3P=CH-(CH_2)p-CO_2H$ (IX)

in which p has the same meaning as in the formula (I'), to yield, after the action of diazomethane, the compound of formula (XXIV):

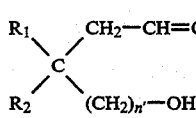 (XXIV)

in which $R_1$, $R_2$, p and n' have the same meaning as in the formula (I'), which is reacted with mesyl chloride in the presence of triethylamine in toluene: to yield the compound of formula (XXV):

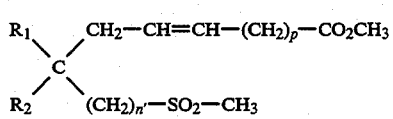 (XXV)

in which $R_1$, $R_2$, p and n' have the same meaning as in the formula (I'), which is reacted with a solution of di-tert-butyl iminodicarbonate in dimethylformamide which has previously been reacted with a suspension of sodium hydride in dimethylformamide, to yield the compound of formula (XXVI):

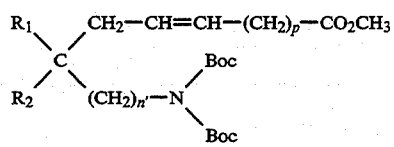 (XXVI)

in which $R_1$, $R_2$, p and n' have the same meaning as in (I'), which is converted to the corresponding amine of formula (XXVII) by reaction in ethereal hydrogen chloride,

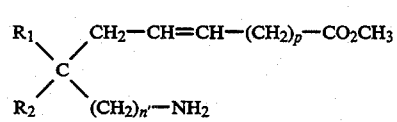 (XXVII)

in which $R_1$, $R_2$, p and n' have the same meaning as in the formula (I'), which is converted to the compound of formula (XXVIII):

$$\begin{array}{c} R_1 \\ \diagdown \\ R_2 \diagup C \diagdown (CH_2)_{n'}-NH-R_3 \end{array} \begin{array}{c} CH_2-CH=CH-(CH_2)_p-CO_2CH_3 \end{array} \quad (XXVIII)$$

in which $R_1$, $R_2$, $R_3$, p and n' have the same meaning as in the formula (I'), by reaction, depending on the nature of $R_3$ either with a halogenated compound of formula (VI) in the presence of triethylamine in toluene:

$$R'_3X \quad (VI)$$

in which X represents a halogen atom and $R'_3$ represents a substituted or unsubstituted phenylsulfonyl radical or an acyl radical, or with an isocyanate of formula $R''-N=C=O$ (VI') in which R'' represents an alkyl radical, and in this case the radical $R_3$ of the formula (VII) is an alkylaminocarbonyl radical, or with an aldehyde of formula $R''_3CHO$ (VI'') in which $R''_3$ is an alkyl radical, to form an imine which is then reduced to the corresponding amine, which is saponified to yield the compound of formula (I/e), a special case of the compounds of formula (I'), $$\begin{array}{c} R_1 \\ \diagdown \\ R_2 \diagup C \diagdown (CH_2)_{n'}-NH-R_3 \end{array} \begin{array}{c} CH_2-CH=CH-(CH_2)_p-CO_2H \end{array} \quad (I/e)$$

in which $R_1$, $R_2$, $R_3$, p and n' have the same meaning as in the formula (I') or of potassium cyanide in dimethyl sulfoxide to yield the compound of formula (XXIX):

$$\begin{array}{c} R_1 \\ \diagdown \\ R_2 \diagup C \diagdown CH_2-CO_2H \end{array} \begin{array}{c} (CH_2)_2-CN \end{array} \quad (XXIX)$$

in which $R_1$ and $R_2$ have the same meaning as in the formula (I'), which is reacted with ethyl chloroformate in acetone in the presence of triethylamine, to yield the compound of formula (XXX):

$$\begin{array}{c} R_1 \\ \diagdown \\ R_2 \diagup C \diagdown CH_2-C-O-CO_2Et \\ \parallel \\ O \end{array} \begin{array}{c} (CH_2)_2-CN \end{array} \quad (XXX)$$

in which $R_1$ and $R_2$ have the same meaning as in the formula (I'), which is subjected to the action of sodium azide in an aqueous medium and then, after heating in toluene, to the action of tert-butanol, to yield the compound of formula (XXXI):

$$\begin{array}{c} R_1 \\ \diagdown \\ R_2 \diagup C \diagdown CH_2-NH-Boc \end{array} \begin{array}{c} (CH_2)_2-CN \end{array} \quad (XXXI)$$

in which $R_1$ and $R_2$ have the same meaning as in the formula (I'), which is reduced to the corresponding aldehyde of formula (XXXII) in the presence of three equivalents of diisobutylaluminum hydride in toluene, $$\begin{array}{c} R_1 \\ \diagdown \\ R_2 \diagup C \diagdown CH_2-NH-Boc \end{array} \begin{array}{c} (CH_2)_2-CHO \end{array} \quad (XXXII)$$

in which $R_1$ and $R_2$ have the same meaning as in the formula (I'), which is reacted with the phosphorus ylide of formula (IX) described above, to yield the compound of formula (XXXIII):

$$\begin{array}{c} R_1 \\ \diagdown \\ R_2 \diagup C \diagdown CH_2-NH-Boc \end{array} \begin{array}{c} (CH_2)_2-CH=CH-(CH_2)_p-CO_2H \end{array} \quad (XXXIII)$$

in which $R_1$, $R_2$ and p have the same meaning as in the formula (I'), the amine function of which is deprotected in ethereal hydrogen chloride, and which then undergoes the same reactions as those described for converting the compound (XXVII) to the compound (XXVIII), to yield the compound of formula (I/f), a special case of the compounds of formula (I), $$\begin{array}{c} R_1 \\ \diagdown \\ R_2 \diagup C \diagdown CH_2-NH-R_3 \end{array} \begin{array}{c} (CH_2)_2-CH=CH-(CH_2)_p-CO_2H \end{array} \quad (I/f)$$

in which $R_1$, $R_2$, $R_3$ and p have the same meaning as in the formula (I'), which compounds of formula (I/e) or (I/f) are reduced, if so desired, by catalytic hydrogenation to yield the compounds of formulae (I/e$_1$) or (I/f$_1$), respectively, special cases of the compounds of formula (I):

$$\begin{array}{c} R_1 \\ \diagdown \\ R_2 \diagup C \diagdown CH_2-CH_2-CH_2-(CH_2)_p-CO_2H \end{array} \begin{array}{c} (CH_2)_{n'}-NH-R_3 \end{array} \quad (I/e_1)$$

$$\begin{array}{c} R_1 \\ \diagdown \\ R_2 \diagup C \diagdown (CH_2)_2-CH_2-CH_2-(CH_2)_p-CO_2H \end{array} \begin{array}{c} CH_2-NH-R_3 \end{array} \quad (I/f_1)$$

in which formulae $R_1$, $R_2$, p and n' have the same meaning as in the formula (I), which compounds of formulae (I/e), (I/e$_1$), (I/f) or (I/f$_1$):

are purified according to standard purification techniques, are separated, where appropriate, into their isomers, according to standard separation techniques, and are converted, if so desired, to their addition salts with a pharmaceutically acceptable acid or base.

The compounds of formula (I) possess very advantageous pharmacological properties. In particular, they are capable of inhibiting platelet aggregation incuded by U46619 (9,11-dideoxy-11α,9α-epoxymethanoprostaglandin F$_{2\alpha}$), a TXA$_2$ receptor agonist, of inhibiting contractions caused by U46619 on guinea pig trachea and of preventing in vivo U46619-induced bronchoconstrictions in guinea pigs. Furthermore, the compounds inhibit TXA$_2$ synthesis in the blood of rabbits.

The subject of the present invention is also pharmaceutical compositions containing as active principle at least one compound of formula (I), alone or in combination with one or more nontoxic, inert excipients or vehicles.

Among the pharmaceutical compositions according to the invention, there may be mentioned, more especially, those which are suitable for oral, parenteral or nasal administration, simple or sugar-coated tablets, sublingual tablets, hard gelatin capsules, troches, suppositories, creams, ointments, skin gels, and the like.

The appropriate dosage varies according to the patient's age and weight, the nature and severity of the condition and also the administration route. The latter can be oral, nasal, rectal or parenteral. Generally speaking, single doses range between 10 and 200 mg for a treatment administered in 1 to 3 doses per 24 hours.

The examples which follow illustrate the invention and in no way limit it.

The starting materials used are known products or products prepared according to known procedures.

EXAMPLE 1

(5Z)-10-[(4-Chlorophenyl)sulfonamido]-8,8-pentamethylene-5-decenoic acid sodium salt Stage A: 4,4-Pentamethylenevalerolactone 372 mmol of 1,1-cyclohexanediacetic anhydride (prepared from the corresponding diacid), dissolved in 300 ml of tetrahydrofuran (THF), are added dropwise at 0° C. to 372 mmol of sodium borohydride suspended in 74 ml of THF. After return of the mixture to room temperature, stirring is maintained for one hour. The mixture is cooled again to 0° C. and 216 ml of 6.9N ethanolic hydrogen chloride are then added to it. The mixture is then brought to reflux for one hour.

After filtration and evaporation, the expected product is obtained in the form of an oil, which is distilled under vacuum.

Yield: 62%

Boiling point : 166°–175° C./20 mmHg

Stage B: 4,4-Pentamethylenevalerolactol

After 65.4 mmol of the product obtained in Stage A have been placed under an inert atmosphere in 200 ml of toluene cooled to −80° C. 87.2 ml of a 15M solution of diisobutylaluminum hydride in toluene are added. When the lactone has disappeared, 50 ml of ethyl acetate are added to the above mixture, followed by 50 ml of water. The mixture is left stirring for one hour at room temperature. After filtration and evaporation of the solvent, the expected product is obtained in the form of a yellow oil.

Yield: 90%

Stage C: Methyl (5Z)-10-hydroxy-8,8-pentamethylene-5-decenoate

After 82.2 mmol of 5-triphenylphosphoniopentanoic acid bromide have been placed under an inert atmosphere in 60 ml of THF, 164.5 ml of a 1M solution of potassium tert-butanolate in THF are added. The mixture is left stirring for one hour at room temperature. It is then cooled to 0° C. and 41.1 mmol of the product obtained in Stage B, dissolved in 80 ml of THF, are added dropwise. After the addition, the mixture is kept stirring at room temperature until the lactol has completely disappeared. After concentration, the aqueous phase is extracted with 100 ml of dichloromethane and then acidified with concentrated hydrochloric acid to pH 1. The medium is then extracted with dichloromethane. The organic phases are combined, dried and evaporated, and yield a residue, which is taken up with ether, the mixture then being filtered. The evaporated liltrate yields 10.6 g of a yellow oil, which is dissolved in 300 ml of ether. An ethereal solution of diazomethane at −40° C. is then added at 0° C. until a yellow coloration persists. The reaction mixture is left for one hour at 0° C. After the addition of a few drops of acetic acid to destroy the excess diazomethane, the mixture is concentrated under vacuum. The expected product is purified by chromatography on a silica column, using a toluene/ethanol (95:5) mixture as eluent.

Yield: 68%

Proton Nuclear Magnetic Resonance (Pyridine-d$_5$/TMS):

Coupling constant between the cis ethylenic protons: J=11.6 Hz

Stage D: Methyl (5Z)-10-methylsulfonyloxy-8,8-pentamethylene-5-decenoate 28 mmol of the compound obtained in Stage C and 36.6 mmol of triethylamine are placed in 100 ml of ether. 33.5 mmol of methanesulfonyl chloride, dissolved in 50 ml of ether, are then added dropwise at room temperature. The expected product is then obtained, after evaporation of the solvent, in the form of a yellow oil.

Yield: 81%

Stage E: Methyl (5Z)-10-[bis(tert-butoxycarbonyl)amino]-8,8-pentamethylene-5-decenoate 50 ml of a solution containing 30 mmol of di-tert-butyl iminodicarbonate in anhydrous dimethylformamide (DMF) are added under an inert atmosphere and at room temperature to a suspension containing 30 mmol of sodium hydride in 30 ml of anhydrous DMF. The mixture is heated to 60° C. for 5 hours with stirring. 22.5 mmol of the compound obtained in Stage D, dissolved in 100 ml of anhydrous DMF, are added and heating is maintained for 4 hours. The medium is acidified with 500 ml of 2N hydrochloric acid and then extracted with dichloromethane. After drying and evaporation of the solvents, the expected product is obtained in the form of a yellow oil.

Yield: 98%

Stage F: Methyl (5Z)-10-amino-8,8-pentamethylene-5-decenoate, chlorhydrate 200 ml of 3.3N ethereal hydrogen chloride are added dropwise at room temperature to a solution containing 22.2 mmol of the product obtained in Stage E in 30 ml of ether. Stirring is maintained for 15 hours. After evaporation of the solvents, the residue is taken up with ether. The expected product is obtained, after filtration and evaporation, in the form of a yellow oil.

Yield: 96%

Stage G: Methyl (5Z)-10-[(4-chlorophenyl)sulfonamido]-8,8-pentamethylene-5-decenoate 4.5 mmol of 4-chlorophenylsulfonyl chloride, dissolved in 30 ml of ether, are added dropwise at room temperature to a solution containing 5.4 mmol of triethylamine and 4.5 mmol of the compound obtained in Stage F in 50 ml of ether. When the reaction is complete, the salts are filtered off and the filtrate is evaporated. The expected product is obtained after purification of the residue by chromatography on a silica column, using a dichloromethane/acetone (95:5) mixture as eluent.

Yield: 53%

Stage H: (5Z)-10-[(4-Chlorophenyl)sulfonamido]-8,8-pentamethylene-5-decenoic acid sodium salt 770 mmol of the product obtained in Stage G are dissolved in 3 ml of methanol in the presence of 3 ml of 1N sodium hydroxide. The solution is concentrated under vacuum and the residue is diluted with 20 ml of water. The aqueous phase is extracted with ether and then acidified with 1N hydrochloric acid solution (pH-1). After extraction with dichloromethane, the organic phases are dried and then evaporated. The residue is diluted with 5 ml of methanol. 7.7 ml of N/10 sodium hydroxide are then added. The mixture is stirred for one hour at room temperature and then evaporated. The expected product crystallizes in ether.

Yield: 100%
Melting point: 145°–147° C.
Proton Nuclear Magnetic Resonance (Pyridine-$d_5$/TMS):
Coupling constant between the cis ethylenic protons: J=11.6 Hz
Elemental microanalysis:

|  | C % | H % | N % | Cl % | S % |
| --- | --- | --- | --- | --- | --- |
| calculated | 56.05 | 6.50 | 3.11 | 7.88 | 7.13 |
| found | 55.77 | 6.83 | 3.31 | 8.15 | 6.79 |

Examples 2 to 5 were obtained according to the same procedure as that described for Example 1, using the corresponding starting materials.

EXAMPLE 2

(4Z)-9-[(4-Chlorophenyl) sulfonamido]-7,7-pentamethylene-4-nonenoic acid sodium salt Melting point: 135°–138° C.
Proton Nuclear Magnetic Resonance (Pyridine-$d_5$/TMS):
Coupling constant between the cis ethylenic protons: J=10.3 Hz
Elemental microanalysis:

|  | C % | H % | N % | Cl % | S % |
| --- | --- | --- | --- | --- | --- |
| calculated | 55.10 | 6.24 | 3.21 | 8.13 | 7.35 |
| found | 55.24 | 6.69 | 3.24 | 8.48 | 7.05 |

EXAMPLE 3

(4Z)-9-[(4-Chlorophenyl) sulfonamido]-7,7-tetramethylene-4-nonenoic acid sodium salt Melting point: 180° C.
Elemental analysis:

|  | C % | H % | N % | Cl % | S % |
| --- | --- | --- | --- | --- | --- |
| calculated | 54.09 | 5.97 | 3.32 | 8.40 | 7.60 |
| found | 54.02 | 6.22 | 3.42 | 8.25 | 7.51 |

EXAMPLE 4

(5Z)-10-[(4-Methylphenyl)sulfonamido]-8,8-pentamethylene-5-decenoic acid sodium salt Melting point: 79°–85° C.
Elemental microanalysis:

|  | C % | H % | N % | S % |
| --- | --- | --- | --- | --- |
| calculated | 61.52 | 7.51 | 3.26 | 7.46 |
| found | 61.33 | 7.79 | 3.35 | 7.39 |

EXAMPLE 5

(5Z)-10-[(4-Bromophenyl)sulfonamido]-8,8-pentamethylene-5-decenoic acid sodium salt Melting point: 130°–133° C.
Elemental microanalysis:

|  | C % | H % | N % | Br % | S % |
| --- | --- | --- | --- | --- | --- |
| calculated | 51.02 | 5.91 | 2.83 | 16.16 | 6.49 |
| found | 50.76 | 6.13 | 2.96 | 16.29 | 6.64 |

EXAMPLE 6

(4Z)-8-[(4-Chlorophenyl) sulfonamido]-7,7-tetramethylene-4-octenoic acid sodium salt Stage A: 1-(2,2-Dimethoxyethyl)cyclopentanecarbonitrile 0.1 mol of cyclopentanecarbonitrile in 50 ml of THF is added in a rapid dropwise manner to a solution, stirred at 78° C. under an argon atmosphere, of 0.1 mol of lithium diisopropylamide (prepared from 0.1 mol of diisopropylamine and 63 ml of 1.6M butyllithium in hexane) in 250 ml of anhydrous THF. The mixture is stirred for 5 minutes at this temperature before adding 0.11 mol of 1-bromo-2,2dimethoxyethane. The mixture is allowed to return to room temperature and is hydrolyzed using 150 ml of water. The medium is allowed to settle, and the aqueous phase is separated and extracted twice with 150 ml of ether. The combined organic phases are washed with 100 ml of aqueous saline solution and 100 ml of water and then dried over magnesium sulfate. The solvents are evaporated off under vacuum and the residual oil is distilled.

Boiling point: 84° C. (p=0.2 mmHg)
Yield: 54%

Stage B: 1-(2,2-Dimethoxyethyl)cyclopentanemethylamine 54 mmol of the product obtained in Stage A, in 100 ml of ether, are added dropwise to 109 mmol of lithium aluminum hydride suspended in 200 ml of ether stirred at room temperature under a nitrogen atmosphere. When all the nitrile has disappeared, 10 ml of ethyl acetate are added to the mixture, followed by 10 ml of water. The mixture is stirred for 1 hour, filtered and dried over MgSO$_4$ and the solvent is evaporated off. The expected product is obtained in an 88% yield.

Stage C: N-[(4-Chlorophenyl) sulfonyl]-1-(2,2-dimethoxyethyl) cyclopentanemethylamine Obtained according to the same procedure as that described in Stage G of Example 1, using the product obtained in the preceding stage as the starting material.
Yield: 96%

Stage D: N-[(4-Chlorophenyl)sulfonyl]-3-hydroxy-2-azaspiro[4.4]nonane

A solution of 31.7 mmol of the product obtained in the preceding stage and 20.1 mmol of para-toluenesulfonic acid in 280 ml of THF and 60 ml of water is brought to reflux for 8 hours. After return of the reaction medium to room temperature, it is concentrated to 4/5 of its volume. The product is extracted with 200 ml of CH$_2$Cl$_2$, and the organic phase is washed with 50 ml of saturated sodium bicarbonate solution, 50 ml of aqueous saline solution and 50 ml of water. After the organic phase has been dried over MgSO$_4$, the solvent is evaporated off under vacuum.

Yield: 63%

Stage E: (4Z)-8-[(4-Chlorophenyl)sulfonamido]-7,7-tetramethylene-4-octenoic acid After 40 mmol of 4-triphenylphosphoniobutanoic acid chloride have been placed under an inert atmosphere in 60 ml of THF, 80 ml of a 1M solution of potassium tert-butanolate in THF are added. The mixture is left stirring for 1 hour at room temperature. It is then cooled to 0° C. and 20 mmol of the product obtained in the preceding stage, dissolved in 40 ml of THF, are added dropwise. After the addition, the mixture is kept stirring at room temperature until the lactam has completely disappeared. After concentration, the aqueous phase is extracted with 100 ml of CH$_2$Cl$_2$ and then acidified with concentrated hydrochloric acid to pH 1. The medium is then extracted with CH$_2$Cl$_2$. The organic phases are combined, dried and evaporated. The oily residue is purified by chromatography on a silica column, using a CH$_2$Cl$_2$/methanol/acetic acid (95:4:1) mixture as eluent. The expected product crystallizes.

Yield: 52%

Melting point: 100° C.

Stage F: (4Z)-8-[(4-Chlorophenyl) sulfonamido]-7,7-tetramethylene-4-octenoic acid sodium salt The product obtained in the preceding stage is diluted with 10 ml of methanol. 10.4 ml of N sodium hydroxide are then added. The mixture is stirred for 1 hour at room temperature and then evaporated. The expected product crystallizes in ether.

Yield: 100%

Proton Nuclear Magnetic Resonance (DMSO-d$_6$):

Coupling constant between the cis ethylenic protons: J=11.5Hz

Elemental microanalysis:

|  | C % | H % | N % | Cl % | S % |
|---|---|---|---|---|---|
| calculated | 53.00 | 5.68 | 3.43 | 8.69 | 7.86 |
| found | 53.40 | 5.73 | 3.55 | 8.72 | 7.63 |

EXAMPLE 7

(4Z)-8-[(4-Chlorophenyl) sulfonamido]-7,7-pentamethylene-4-octenoic acid sodium salt Prepared according to the same procedure as that described in Example 6.

Melting point: 194° C.

Yield: 80%

Proton Nuclear Magnetic Resonance (DMSO-d$_6$)

Coupling constant between the cis ethylenic protons: J=11.8 Hz

Elemental microanalysis:

|  | C % | H % | N % | Cl % | S % |
|---|---|---|---|---|---|
| calculated | 54.09 | 5.97 | 3.32 | 8.40 | 7.60 |
| found | 54.68 | 6.18 | 3.56 | 8.67 | 7.44 |

EXAMPLE 8

(5Z)-9-[(4-Chlorophenyl)sulfonamido]-8,8-tetramethylene-5-nonenoic acid sodium salt Prepared according to the procedure described for Example 6.

Yield: 66%

Melting point: 124%

Proton Nuclear Magnetic Resonance (CDCl$_3$)

Coupling constant between the cis ethylenic protons: J=11.6 Hz

Elemental microanalysis:

|  | C % | H % | N % | Cl % | S % |
|---|---|---|---|---|---|
| calculated | 54.09 | 5.97 | 3.32 | 8.40 | 7.60 |
| found | 53.78 | 6.05 | 3.61 | 8.55 | 7.46 |

EXAMPLE 9

(4Z)-9-[(4-Chlorophenyl)sulfonamido]-8,8-tetramethylene-4-nonenoic acid sodium salt Prepared according to the procedure described in Example 6.

Yield: 63%

Proton Nuclear Magnetic Resonance (DMSO-d$_6$)

Coupling constant between the cis ethylenic protons: J=11.6 Hz

Elemental microanalysis:

|  | C % | H % | N % | Cl % | S % |
|---|---|---|---|---|---|
| calculated | 54.09 | 5.97 | 3.32 | 8.40 | 7.60 |
| found | 54.27 | 6.41 | 3.46 | 8.39 | 7.10 |

EXAMPLE 10

(4Z)-8-[(4-Chlorophenyl)sulfonamido]-8,8-tetramethylene-4-octenoic acid sodium salt Stage A: Methyl 1-(3,3-dimethoxypropyl)cyclopentanecarboxylate Prepared according to a procedure identical to Stage A of Example 6, starting from methyl cyclopentanecarboxylate and 3-bromopropionaldehyde dimethyl acetal, with a 72% yield.

Stage B: 1-(3,3-Dimethoxypropyl)cyclopentanecarboxylic acid 94 mmol of the product prepared in the preceding stage are diluted in 100 ml of methanol. After 25 ml of 35% sodium hydroxide have been added, the medium is heated to reflux for 2 hours; after return of the medium to room temperature, it is then extracted with 200 ml of CH$_2$Cl$_2$. The aqueous phase is acidified to pH 5 with N HCl and is extracted 3 times using 100 ml of CH$_2$Cl$_2$. The combined organic phases, dried over magnesium sulfate, are evaporated under vacuum.

Yield: 88%

Stage C: N-Benzyloxycarbonyl-1-(3,3-dimethoxypropyl) cyclopentylamine

A solution containing 23.1 mmol of the product prepared in the preceding stage, 25.4 mmol of diphenylphosphoryl azide (DPPA) and 27.7 mmol of triethylamine in 100 ml of anhydrous benzene is brought to reflux for 3 hours. After concentration of the solvent, the residue is chromatographed on silica, employing a CH₂Cl₂/acetone (95:5) mixture as eluent. 21.9 mmol (95%) of an oil are thereby recovered, which oil possesses an absorption band in IR at 2256 cm$^{-1}$. This oil is diluted with 25 ml of anhydrous DMF. 21.9 mmol of benzyl alcohol and 21.9 mmol of CuCl are added and the reaction medium is stirred for 45 minutes at room temperature. The medium is then diluted with 100 ml of ether, washed with 50 ml of water and 25 ml of aqueous saline solution and then dried over magnesium sulfate. After concentration of the solvents, the product is purified by chromatography on silica, using a CH₂Cl₂/acetone (95:5) mixture as eluent.

Yield: 73%

Stage D: 1-(3,3-Dimethoxypropyl)cyclopentylamine

The product obtained in the preceding step, diluted in 50 ml of methanol, is stirred at room temperature under a hydrogen atmosphere in the presence of 100 mg of palladium on charcoal (content 10%). The medium is filtered and the solvent is concentrated. The expected product is a colorless oil.

Yield: 100%

Stage E: N-[(4-Chlorophenyl)sulfonyl]-1-(3,3-dimethoxypropyl)cyclopentylamine

Prepared according to the procedure described in Stage G of Example 1.

Yield: 83%

Stage F: N-[(4-Chlorophenyl)sulfonyl]-2-hydroxyl-1-azaspiro[4.4]nonane

Prepared according to the procedure described in Stage D of Example 6.

Yield: 70%

Stage G: (4Z)-8-[(4-Chlorophenyl)sulfonamido]-8,8-tetramethylene-4-octenoic acid Prepared according to the procedure described in Stage E of Example 6.

Yield: 68%

Stage H: (4Z)-8-[(4-Chlorophenyl)sulfonamido]-8,8-tetramethylene-4-octenoic acid sodium salt Prepared according to the procedure described in Stage F of Example 6.

Yield: 100%

Melting point: 99.5° C.

Elemental microanalysis:

|  | C % | H % | N % | Cl % | S % |
|---|---|---|---|---|---|
| calculated | 53.00 | 5.68 | 3.43 | 8.69 | 7.86 |
| found | 52.91 | 5.78 | 3.74 | 8.82 | 7.98 |

EXAMPLE 11

(5Z)-9-[(4-Chlorophenyl)sulfonamido]-9,9-tetramethylene-5-nonenoic acid sodium salt Obtained according to the same procedure as that described in Example 10, using the corresponding starting materials.

Melting point: 163° C.

Proton Nuclear Magnetic Resonance (DMSO-d₆)

Coupling constant between the cis ethylenic protons: J=10.8 Hz

Elemental microanalysis:

|  | C % | H % | N % | Cl % | S % |
|---|---|---|---|---|---|
| calculated | 54.09 | 5.97 | 3.32 | 8.40 | 7.60 |
| found | 53.59 | 5.95 | 3.60 | 8.65 | 7.36 |

EXAMPLE 12

(5Z)-10-[(4-Chlorophenyl)sulfonamido]-8,8-tetramethylene-5-decenoic acid sodium salt Prepared according to the same procedure as that described in Example 1, using the corresponding starting materials.

Melting point: 117° C.

Proton Nuclear Magnetic Resonance (DMSO-d₆)

Coupling constant between the cis ethylenic protons: J=10.8 Hz

Elemental microanalysis:

|  | C % | H % | N % | Cl % | S % |
|---|---|---|---|---|---|
| calculated | 55.10 | 6.24 | 3.21 | 8.13 | 7.35 |
| found | 55.67 | 6.70 | 3.22 | 7.86 | 7.55 |

EXAMPLE 13

(4Z)-9-[(1-Naphthyl)sulfonamido]-7,7-tetramethylene-4-nonenoic acid sodium salt

Prepared according to the procedure described in Example 1, using the corresponding starting materials.

Melting point: 141°–142° C.

Elemental microanalysis:

|  | C % | H % | N % | S % |
|---|---|---|---|---|
| calculated | 63.14 | 6.45 | 3.20 | 7.33 |
| found | 62.82 | 6.64 | 3.38 | 7.48 |

EXAMPLE 14

(4Z)-10-[(4-Chlorophenyl)sulfonamido]-8,8-tetramethylene-4-decenoic acid sodium salt Stage A: 1-(3,3-Dimethoxypropyl)cyclopentanemethanol A solution of 0.25 mol of the compound prepared in Stage A of Example 10 in 200 ml of ether is added dropwise to a suspension, stirred at 0° C., of 0.25 mol of lithium aluminum hydride in 200 ml of ether. When the addition is complete, the reaction medium is allowed to return to room temperature, and is then stirred for 4 hours at this temperature before being hydrolyzed by adding 20 ml of water. The salts are filtered off and washed twice with ether, and the filtrate is dried and concentrated.

Yield: 77%

Stage B 1-(Methylsulfonyloxymethyl)cyclopentanepropionaldehyde dimethyl acetal

Prepared from the above compound according to the same procedure as that described in Stage D of Example 1.

Yield: 95%

Stage C: 1-(3,3-Dimethoxypropyl)cyclopentaneacetonitrile

A solution containing 15.4 mmol of the product prepared in the preceding stage and 16.9 mmol of potassium cyanide in 300 ml of DMSO is heated to 100° C. for 15 hours. The cooled medium is hydrolyzed with 600 ml of ice-cold water and is extracted with 3 times 150 ml of ethyl acetate. The combined organic phases are dried over magnesium sulfate and, after evaporation of the solvents, the expected product is purified by chromatography on silica, using a toluene/acetone (95:5) mixture as eluent.

Yield: 60%

Stage D: 1-(3,3-Dimethoxypropyl)cyclopropaneethylamine

Prepared according to the procedure described in Stage B of Example 6.

Yield: 90%

Stage E: N-[(4-Chlorophenyl)sulfonyl]-1-(3,3-dimethoxypropyl)cyclopentaneethylamine Prepared according to the procedure described in Stage G of Example 1.

Yield: 89%

Stage F: N-[(4-Chlorophenyl)sulfonyl]-7-aza-8-hydroxyspiro[4.6]undecane

Prepared according to a procedure identical to Stage D of Example 6.

Yield: 80%

Stage G: (4Z)-10-[(4-Chlorophenyl)sulfonamido]-8,8-tetramethylene-4-decenoic acid Prepared according to the procedure described in Stage E of Example 6.

Yield: 78%

Stage H: (4Z)-10-[(4-Chlorophenyl)sulfonamido]-8,8-tetramethylene-4-decenoic acid sodium salt Prepared according to the procedure described in Stage F of Example 6.

Yield: 91%

Melting point: 105° C.

Proton Nuclear Magnetic Resonance (DMSO-$d_6$)

Coupling constant between the cis ethylenic protons: J=11.1 Hz

Elemental microanalysis:

|  | C % | H % | N % | Cl % | S % |
|---|---|---|---|---|---|
| calculated | 55.10 | 6.24 | 3.21 | 8.13 | 7.35 |
| found | 55.40 | 6.51 | 3.29 | 7.81 | 7.18 |

EXAMPLE 15

(4Z)-6-{1-[2-(4-Chlorophenyl)sulfonamidoethyl]-4-ter-butyl-1-cyclohexyl}-4-hexanoic acid sodium salt Stage A: (4-tert-Butylcyclohexylidene)cyanoacetic, ethyl ester A mixture of 0.13 mol of 4-tert-butylcyclohexanone, 0.195 mol of ethyl cyanoacetate, 6 ml of acetic acid, 5 g of ammonium acetate and 200 ml of benzene is brought to reflux for 4 hours in a round-bottomed flask surmounted by a Dean and Stark apparatus. After return of the reaction medium to room temperature, it is concentrated under vacuum, and the residue is purified by chromatography on silica, using a $CH_2Cl_2$/hexane (70:30) mixture as eluent.

Yield: 90%

Melting point: 43° C.

Stage B: 9-tert-Butyl-1,5-dicyano-2,4-dioxo-3-azaspiro[5.5]undecane

A solution of 0.116 mol of cyanoacetamide in 200 ml of ethanol is run dropwise into a solution, stirred at room temperature, of 0.116 mol of sodium ethanolate in 200 ml of ethanol. The suspension is stirred for 1 hour at room temperature before adding 0.116 mol of the compound obtained in the preceding stage in small portions. The resulting solution is stirred for 12 hours at room temperature before being hydrolyzed using 300 ml of water. The medium is then acidified to pH 1 by the slow addition of the requisite amount of 3N hydrochloric acid. The precipitate is filtered off and washed with a minimum amount of alcohol and then of diisopropyl ether.

Yield: 95%

Melting point: 248° C.

Stage C: 4-tert-Butyl-1,1-cyclohexanediacetic acid

A suspension of 0.11 mol of the compound prepared in the preceding stage in 350 ml of water, 350 ml of concentrated hydrochloric acid and 1050 ml of glacial acetic acid is brought to reflux for 5 days. The medium is concentrated under vacuum, the residue, taken up in 500 ml of an ether/ethanol (50:50) mixture is filtered off, the filtrate is concentrated and the solid residue is taken up in 150 ml of pentane.

Yield: 85%

Melting point: 178° C.

Stage D: 9-tert-Butyl-3-oxaspiro[5.5]undecane-2,4-dione

A solution of 0.09 mol of the compound prepared in the preceding stage in 300 ml of acetic anhydride is brought to reflux for 12 hours. After concentration under vacuum, the crystallized residue is taken up twice in 200 ml of pentane.

Yield: 76%

Melting point: 110°–112° C.

Stage E: 9-tert-Butyl-2-oxo-3-oxaspiro[5.5]undecane, mixture of isomers

Prepared according to the procedure of Stage A of Example 1; the crude oil recovered is crystallized in pentane to yield, after filtration, the isomer 1.

Yield: 52%

Melting point: 130° C.

The filtrate is concentrated to yield the isomer 2.

Yield: 28%

Melting point: 54° C.

Stage F: 9-tert-Butyl-2-hydroxy-3-oxaspiro[5.5]undecane, isomer 1

Prepared from the isomer 1 prepared above, according to a procedure identical to that used in Stage B of Example 1.

Yield: 59%

Melting point: 143° C.

Stage G: Methyl (4Z)-6-[4-tert-butyl-1-(2-hydroxyethyl)-1-cyclohexyl]-4-hexanoate, isomer 1

Prepared according to a procedure identical to that of Stage C of Example 1.

Yield: 90%

Proton Nuclear Magnetic Resonance (CDCl$_3$):

Coupling constant between the cis ethylenic protons: J=10.8 Hz

Stage H: Methyl (4Z)-6-[4-tert-butyl-1-(2-methylsulfonyl-oxyethyl)-1-cyclohexyl]-4-hexenoate, isomer 1

Prepared according to a procedure identical to that of Stage D of Example 1.

Yield: 94%

Stage I: Methyl (4Z)-6-}4-tert-butyl-1-[2-bis(tert- butoxycarbonyl)aminoethyl]-1-cyclohexyl}-4- hexenoate, isomer 1

Prepared according to the same procedure as that used in Stage E of Example 1.

Yield: 61%

Stage J: Methyl (4Z)-6-[4-tert-butyl-1-(2-aminoethyl)-1-cyclohexyl]-4-hexenoate hydrochloride, isomer 1

Prepared according to a procedure identical to that used in Stage F of Example 1.

Yield: 100%

Stage K: Methyl (4Z)-6-}4-tert-butyl-1-[2-(4-chlorophenyl) sulfonamidoethyl]-1-cyclohexyl}-4- hexenoate, isomer 1

Prepared according to a procedure identical to that used in Stage G of Example 1.
Yield: 78%

Stage L: (4Z)-6-}4-tert-Butyl-1-[2-(4-chlorophenyl)sulfonamido-ethyl]-1-cyclohexyl}-4-hexenoic acid sodium salt, isomer 1

Prepared according to a procedure identical to that used in Stage H of Example 1.
Yield: 58%
Melting point: 191° C.
Elemental microanalysis:

|  | C % | H % | N % | Cl % | S % |
|---|---|---|---|---|---|
| calculated | 58.58 | 7.17 | 2.85 | 7.21 | 6.52 |
| found | 58.15 | 7.27 | 3.04 | 7.26 | 6.89 |

EXAMPLE 16

(4Z)-6-{1-[2-(4-Chlorophenyl)sulfonamidoethyl]-1-indanyl}-4-hexenoic acid sodium salt Prepared according to the same procedure as that described in Example 15, using the corresponding starting materials.
Yield: 98%
Melting point: 75°-80° C.
Proton Nuclear Magnetic Resonance (DMSO-$d_6$)
Coupling constant between the cis ethylenic protons: J=10.8 Hz
Elemental microanalysis:

|  | C % | H % | N % | Cl % | S % |
|---|---|---|---|---|---|
| calculated | 58.78 | 5.36 | 2.98 | 7.54 | 6.82 |
| found | 58.67 | 5.68 | 2.90 | 7.50 | 6.54 |

EXAMPLE 17

(5Z)-7-{1-[2-(4-Chlorophenyl)sulfonamidoethyl]-1-indanyl}-5-heptenoic acid sodium salt Prepared according to the same procedure as that described in Example 15, using the corresponding starting materials.
Yield: 91%
Melting point : 95°-105° C.
Proton Nuclear Magnetic Resonance (DMSO-$d_6$)
Coupling constant between the cis ethylenic protons: J=10.8 Hz
Elemental microanalysis:

|  | C % | H % | N % | Cl % | S % |
|---|---|---|---|---|---|
| calculated | 59.56 | 5.62 | 2.89 | 7.33 | 6.62 |
| found | 59.69 | 5.90 | 3.03 | 7.33 | 6.93 |

EXAMPLE 18

(4Z)-6-}2-[2-(4-Chlorophenyl)sulfonamidoethyl]-1,2,3,4-tetrahydro-2-naphthyl}-4- hexenoic acid sodium salt Stage A: 1,2,3,4 Tetrahydronaphthalene-2-spiro-4'-(3',5'-dicyano-2',6'-dioxopiperidine) ammonium salt A mixture of 0.13 mol of 2-tetralone and 0.26 mol of ethyl cyanoacetate in 250 ml of ammoniacal ethanol is maintained at 0° C. for 48 hours. The solid is filtered off, washed using a minimum amount of ethanol and then with ether and dried.
Yield: 31%

The remainder of the synthesis is identical to that used for Example 15.
Yield: 72%
Melting point: 160°-161° C.
Proton Nuclear Magnetic Resonance (DMSO-$d_6$):
Coupling constant between the cis ethylenic protons: J=10.8 Hz
Elemental microanalysis:

|  | C % | H % | N % | Cl % | S % |
|---|---|---|---|---|---|
| calculated | 59.56 | 5.62 | 2.89 | 7.33 | 6.62 |
| found | 59.57 | 5.48 | 3.07 | 7.28 | 6.64 |

EXAMPLE 19

(4Z)-6-{2-[2-(4-Chlorophenyl)sulfonamidoethYl]-2-indanyl}-4-hexenoic acid sodium salt Stage A: Cyanoindan-2-ylidene acetic acid, ethyl ester Prepared from 2-indanone and ethyl cyanoacetate according to a procedure identical to that used in Stage A of Example 15.
Yield: 68%
Melting point: 116° C.

Stage B: 2-Carboxy-2-indaneacetic acid

A solution of 0.2 mol of potassium cyanide in 310 ml of water is added to a suspension of 0.25 mol of the compound prepared in the preceding stage in 310 ml of ethanol. As soon as the medium has become homogeneous, it is brought to reflux for ½ hour. The reaction medium is concentrated, and 220 ml of glacial acetic acid and 450 ml of concentrated hydrochloric acid are added to the residue. The reaction medium is brought to reflux for 48 hours. It is concentrated, the residue obtained is diluted in 150 ml of water and the medium is extracted using twice 100 ml of ethyl acetate. The combined organic phases are washed with 5N sodium hydroxide. The aqueous phase is acidified to pH 1 with concentrated hydrochloric acid and the precipitate is filtered off.
Yield: 67%
Melting point: 165° C.

Stages C to J are identical to Stages D to K of Example 15.
Yield: 70%
Melting point: 100°-105° C. (decomposition)
Proton Nuclear Magnetic Resonance (DMSO-$d_6$):
Coupling constant between the cis ethylenic protons: J=11.1 Hz

EXAMPLE 20

(5Z)-7-{[2-(4-Chlorophenyl)sulfonamidoethyl]-2-indanyl}-5-heptenoic acid sodium salt Prepared according to the process described in Example 23.
Yield: 76%
Melting point: 85°-89° C.
Proton Nuclear Magnetic Resonance (DMSO-$d_6$):
Coupling constant between the cis ethylenic protons: J=11.1 Hz

EXAMPLE 21

6-{4-[2-(4-Chlorophenyl)sulfonamidoethyl]-1-(4-cholorophenylsulfonyl)-4-piperidyl}4-hexenoic acid sodium salt Prepared according to the process described in Example 1.

Pharmacoloqical study of the compounds of the invention

EXAMPLE 22

Platelet Aggregation in Rabbits

Rabbits (2–3 kg) are anesthetized with pentobarbital sodium (30 mg/kg i.v.). After cannulation of the left carotid artery, blood is withdrawn onto sodium citrate (0.109M) (1 vol. of citrate per 9 vol. of blood). Platelet-rich plasma (PRP) is obtained by centrifugation (20° C.) at 250 g for 20 minutes, and platelet-poor plasma (PPP) by centrifugation at 1000 g (10 min). The number of platelets (PL) in the PRP is adjusted to 300–350,000 PL/mm$^3$ by dilution with autologous PPP. The PRP is stored at the temperature of the room until the time of the test, and is used within 4 hours following withdrawal from the animal.

Platelet aggregation is carried out at 37° C. in siliconed glass tubes using an aggregometer. The PRP and the PL are stirred at 1000 rpm (revolutions per minute). In order to study the activity of thromboxane antagonists, the PRP is incubated for 1 min at 37° C., and the antagonist is then added for a period of 3 min before addition of the agonist U46619 (1.2 μM). The final volume in the measuring cell is then 250 μl. The intensity of platelet aggregation is established by taking the maximum amplitude of aggregation plots and is expressed as a percentage light transmission (% T). The activity of the antagonists is expressed as IC50, that is to say the concentration of the substance which induces a 50% inhibition of the aggregation response induced by U46619.

In this test, IC$_{50}$ values of the compounds of Examples 2 and 6 are equal to 2 10$^{-7}$M.

EXAMPLE 23

Platelet Aggregation in Dogs

After anesthesia of the animal with pentobarbital sodium (30 mg/kg i.v.), arterial blood is withdrawn onto sodium citrate (0.109M) (1 vol. of citrate per 9 vol. of blood). Platelet-rich plasma (PRP) is obtained after centrifugation (20° C.) at 200 g for 10 minutes. The number of platelets in the PRP is 300,000 PL/mm$^3$ on average. The PRP is stored at the temperature of the room until the time of the test, and is used within 4 hours following withdrawal from the animal.

Dog platelets respond weakly to U46619 alone. The addition of adrenaline, which does not induce aggregation by itself, enables a larger aggregation response to U46619 to be obtained. The PRP is incubated at 37° C. in the presence of the test antagonist for 3 minutes. Aggregation is then obtained by the addition of adrenaline (10 μM) followed by that of U46619 (1.2 μM) 30 seconds later. The effect of the antagonists is measured, and the IC$_{50}$ is determined as the concentration of the antagonist needed to produce a 50% inhibition of the aggregation responses to U46619+adrenaline.

In this test, the IC$_{50}$ values of the compounds are as follows:

Example 1 1.4×10$^{-7}$M
Example 2 1.2×10$^{-7}$M
Example 3 6×10$^{-8}$M
Example 4 2×10$^{-7}$M
Example 5 1.4×10$^{-7}$M
Example 12 1.5×10$^{-7}$M

EXAMPLE 24

Platelet Aggregation in Man

Venous blood is obtained from human volunteers who have not taken aspirin for at least 14 days prior to the experiment. The blood is withdrawn onto sodium citrate (0.109M) (1 vol. of citrate to 9 vol. of blood). Platelet-rich plasma (PRP) is obtained after centrifugation (20° C.) at 200 g for 10 minutes. The number of platelets is 250,000 PL/mm$^3$ on average. The PRP is stored at the temperature of the room until the time of the test, and is used within 2 hours following withdrawal from the subject. The antagonists are tested according to the procedure described in Example 22.

In this test, the IC50 values of the compounds are as follows:

Example 2 2 10$^{-7}$M
Example 3 8 10$^{-8}$M
Example 6 8 10$^{-8}$M
Example 7 3 10$^{-7}$M
Example 8 3 10$^{-7}$M
Example 9 2 10$^{-7}$M
Example 12 5 10$^{-7}$M
Example 14 8 10$^{-7}$M

EXAMPLE 25

Determination of the pA$_2$ Values on Guinea Pig Trachea

Male albino guinea pigs weighing 400–500 grams were sacrificed by a blow to the back of the neck and by cervical elongation. The throat is opened and the trachea is rapidly removed and then cut into two-cartilage rings. These rings are mounted between two hooks in measuring cells thermostated at 37° C. containing physiological fluid (composition in mM:NaCl 118 ; NaHCO$_3$ 25; Glucose 10; KCl 4.7; CaCl$_2$ 1.25; MgSO$_4$ 1.19; KH$_2$PO$_4$ 1.14). A 95% 0$_2$/5% CO$_2$ mixture is bubbled through the physiological solution. The lower hook represents the fixed point while the upper hook is connected to an isometric-force gauge. The tissues are placed under a baseline tension of 3.5 grams. The test pharmacological substances are prepared immediately before use. The drugs are solubilized in water or in dimethyl sulfoxide. After mounting, the preparations are left at rest for 90 minutes, rinses being carried out every 30 minutes. After readjustment of the baseline tension, a contraction caused by a single dose of agonist (U46619 ; 10$^{-5}$M) is produced in order to make the contractions which follow consistent. After washing and return to the baseline, a first effect/concentration curve is established by adding cumulative doses of U46619 (10$^{-9}$M to 10$^{-5}$M; the spacing between the doses is on a semi-log basis). This first experiment enables the "control" 50% effective concentration (EC50) to be calculated.

This EC$_{50}$ is routinely calculated in the following manner: the tension values are first converted to percentages relative to the maximum effect, these percentages then being plotted on a graph with the percentages as ordinates and the log (concentration) values as abscissae. A linear regression is then carried out on the points lying between 10% and 90% (which corresponds to the linear portion of the sigmoid curve). The concentration corresponding to half the maximum effect (50%) may be readily calculated using the parameters of the linear plot.

After washing and return to the baseline, the organ is brought into contact with the antagonist (8 different concentrations for each organ) for 20 minutes. A second effect/concentration curve is then established in the presence of the antagonist, and the "treated" $EC_{50}$ can then be calculated. All the elements enabling the $pA_2$ (competitive antagonism) or $pD_2$ (non-competitive antagonism) to be calculated are thereby obtained. The $pA_2$ (which represents the negative logarithm of the antagonist concentration in the presence of which twice as much agonist is required in order to obtain the same effect) is determined by plotting on a graph the values of $\log((L/1)-1)$ with respect to log (antagonist concentration), where L=effect in presence of antagonist and 1=control effect.

In this test, the $pA_2$ values of the compounds of the invention are as follows:
Example 1: 9.4
Example 2: 8.4
Example 3: 9.3
Example 4: 8.5
Example 5: 8.2
Example 6: 9.14
Example 7: 9.4
Example 8: 9.63
Example 9: 9.08
Example 10: 7.65
Example 11: 7.70
Example 12: 8.98
Example 16: 8.40

EXAMPLE 26

IC50 on Tracheal Pressure in Guinea Pigs

Male albino guinea pigs (350–400 g) subjected to an 18-hour water diet are anesthetized with ethyl carbamate (1.25 g/kg i.p.). A catheter is introduced into the carotid artery in order to measure the arterial blood pressure by means of a pressure cell. A second catheter is introduced into the jugular vein and is used to inject the pharmacological substances. The trachea is cannulated and the guinea pig is placed in assisted respiration by means of a respirator. The animal's temperature is maintained at 37° C. using a thermostatic blanket. A needle pushed in the tracheal cannula is connected to a pressure cell and enables the tracheal pressure to be recorded.

The guinea pigs are pretreated with d-tubocurarine (1 mg/kg i.v.) and with indomethacin (10 mg/kg i.v.). When injected at a dose of 2 μg/kg i.v., U46619 causes a bronchoconstriction which leads to an increase in tracheal pressure and induces an increase in arterial blood pressure. The responses to U46619 are reversible and reproducible if the injections are carried out every 10 minutes.

The thromboxane receptor antagonists are injected 5 minutes before the injections of U46619. The dose of antagonist that inhibits by 50% the increase in tracheal pressure caused by U46619 is determined ($IC_{50}$).

In this test, the IC50 values of the compounds of the invention are as follows:
Example 1: 27 μg/kg
Example 2: 120 μg/kg
Example 3: 19 μg/kg
Example 4: 105 μg/kg
Example 5: 66 μg/kg
Example 6: 21 μg/kg
Example 7: 20 μg/kg
Example 8: 7 μg/kg
Example 9: 11 μg/kg
Example 12: 9 μg/kg

EXAMPLE 27

Pharmaceutical Composition

Preparation formula for 1000 tablets containing a 10 mg dose

| Compound of Example 2 | 10 g |
|---|---|
| Hydroxypropylcellulose | 2 g |
| Wheat starch | 10 g |
| Lactose | 100 g |
| Magnesium stearate | 3 g |
| Talc | 3 g |

We claim:

1. A compound selected from those of formula (I):

$$\begin{array}{c} R_1 \diagdown \phantom{C} \diagup (CH_2)_n-NHR_3 \\ C \\ R_2 \diagup \phantom{C} \diagdown (CH_2)_m-R_4 \end{array} \quad (I)$$

in which:
$R_1$ or $R_2$, which may be identical or different, with the carbon atom to which they are attached, form a $C_4$-$C_7$ cycloalkyl ring, unsubstituted or substituted with linear or branched $C_1$-$C_6$ alkyl, a benzo $C_4$-$C_7$ cycloalkyl ring-system, or a 4-piperidyl ring, unsubstituted or substituted on the nitrogen of the piperidine with phenylsulfonyl which is itself unsubstituted or substituted with one or more halogen or alkyl,
$R_3$ represents
phenylsulfonyl, unsubstituted or substituted on the phenyl ring with halogen or methyl, or
naphthylsulfonyl,
$R_4$ represents one of the radicals:

$$-CH=CH-(CH_2)_p-CO_2H$$

or $$-CH_2-CH_2-(CH_2)_p-CO_2H$$

in which p is equal to 0, 1, 2 or 3, n and m, which may be identical or different, represent 0, 1 or 2,
its isomers, enantiomers, diastereoisomers and epimers as its addition salts with a pharmaceutically acceptable acid or base.

2. A compound of claim 1, in which $R_3$ represents phenylsulfonyl, unsubstituted or substituted on the phenyl ring.

3. A compound of claim 1, in which $R_4$ represents $-CH=CH-(CH_2)p-CO_2H$ in which p is equal to 0, 1, 2 or 3.

4. A compound of claim 3, in which the substituents attached to the unsaturated carbons of the double bond of the radical $R_4$ are in the cis configuration with respect to each other.

5. A compound of claim 1, in which $R_1$ and $R_2$, with the carbon atom to which they are attached, form a substituted or unsubstituted $C_4$–$C_7$ cycloalkyl ring.

6. A compound of claim 1 which is (4Z)-8-[(4-chlorophenyl)sulfonamido]-7,7-tetramethylene-4-octenoic acid.

7. A compound of claim 1 which is (5Z)-9-[(4-chlorophenyl)sulfonamido]-8,8-tetramethylene-5-nonenoic acid.

8. A compound of claim 1 which is (4Z)-9-[(4-chlorophenyl)sulfonamido]-8,8-tetramethylene-4-nonenoic acid.

9. A compound of claim 1 which is (5Z)-10-[(4-chlorophenyl)sulfonamido]-8,8-tetramethylene-5-decenoic acid.

10. A method for treating an animal or human living body afflicted with a condition requiring a thromboxane $A_2$ receptor antagonist or a thromboxane $A_2$ synthase inhibitor comprising the step of administering to the living body an amount of a compound of claim 1 which is effective for alleviation of said condition.

11. A pharmaceutical composition useful as a thromboxane $A_2$ receptor antagonist or synthase inhibitor, comprising as active principle an effective amount of a compound as claimed in claim 1, together with one or more pharmaceutically-acceptable excipients or vehicles.

* * * * *

UNITED STATES PATENT AND TRADEMARK OFFICE
CERTIFICATE OF CORRECTION

PATENT NO. : 5,436,343
DATED : July 25, 1995
INVENTOR(S) : Gilbert Lavielle, Patrick Hautefaye, Michel Laubie, Tony Verbeuren It is certified that error appears in the above-indentified patent and that said Letters Patent is hereby corrected as shown below:

```
TITLE PAGE, ITEM [57], ABSTRACT, line 6; "(C₁ C₆)" should read
     -- (C₁-C₆) --
Column  1, line 56; "(C₆-C₆)" should read -- (C₁-C₆) --
Column  1, line 58; "(C₆-C₆)" should read -- (C₁-C₆) --
Column  1, line 59; "(C₆-C₆)" should read -- (C₁-C₆) --
Column  1, line 63; "(C₆-C₆)" should read -- (C₁-C₆) --
Column  2, line  4; "(C₆-C₆)" should read -- (C₁-C₆) --
Column  2, line  8; "(C₆-C₆)" should read -- (C₁-C₆) --
Column  2, line 21; "methanesu/-" should read -- methanesul- --
Column  3, line 22; insert a -- * -- at the beginning of the
     line before "with".
Column  3, line 29; insert a -- * -- at the beginning of the
     line before "with".
Column  3, line 33; insert a -- * -- at the beginning of the
     line before "an".
Column  8, line 68; "(XXX1II)" should read -- (XXXIII) --
Column 12, line  4; "liltrate" should read -- filtrate --
Column 16, line  3; insert a -- ) -- at the end of the line.
Column 16, line  4; delete the ")" at the beginning of the line.
Column 18, line 22; insert a ")" at end of the line.
Column 18, line 23; delete the ")" at the beginning of the line.
Column 18, line 37; insert a ")" at the end of the line.
Column 18, line 38; delete the ")" at the beginning of the line.
Column 18, line 54; "Stage B" should read -- Stage B: --
Column 20, line 59; "-6-}4-tert-" should read -- -6-{4-tert- --
Column 21, line  2; "-6-}4-tert-" should read -- -6-{4-tert- --
Column 21, line  8; "-6-}4-tert-" should read -- -6-{4-tert- --
Column 21, line 63; "-6-}2-[2-(4-" should read
     -- -6-{2-[2-(4- --
```

UNITED STATES PATENT AND TRADEMARK OFFICE
CERTIFICATE OF CORRECTION

PATENT NO. : 5,436,343
DATED : July 25, 1995
INVENTOR(S) : Gilbert Lavielle, Patrick Hautefaye, Michel Laubie, Tony Verbeuren It is certified that error appears in the above-indentified patent and that said Letters Patent is hereby corrected as shown below:

Column 21, line 67; "1,2,3,4" should read -- 1,2,3,4- --
Column 22, line 23; "sulfonamidoethYL]" should read -- sulfonamidoethyl] --
Column 23, line 37; "IC50" should read -- $IC_{50}$ --
Column 24, line 21; "IC50" should read -- $IC_{50}$ --
Column 24, line 44; "02/5%" should read -- $O_2$/5% --
Column 24, line 61; "(EC50)" should read -- ($EC_{50}$) --
Column 25, line 38; "$IC_{so}$" should read -- $IC_{50}$ --
Column 25, line 65; "IC50" should read -- $IC_{50}$ --
Column 26, line 57; "as its" should read -- ,and its --
   also, insert a hyphen "-" between the words "pharmaceutically" and "acceptable"
Column 28, line 7; insert a comma "," after " inhibitor "

Signed and Sealed this

Seventeenth Day of October, 1995

Attest:

BRUCE LEHMAN

*Attesting Officer*  *Commissioner of Patents and Trademarks*